United States Patent

Van Daele et al.

[11] Patent Number: 5,556,886
[45] Date of Patent: Sep. 17, 1996

[54] HIV-INHIBITING BENZENEACETAMIDE DERIVATIVES

[75] Inventors: Georges H. Van Daele, Turnhout; Marc G. Verdonck, Gierle; Jean-Paul R. Bosmans, Kortrijk-Marke; Paul A. Janssen, Vosselaar, all of Belgium

[73] Assignee: Janssen Pharmaceutica N.V., Beerse, Belgium

[21] Appl. No.: 411,039

[22] Filed: Mar. 27, 1995

Related U.S. Application Data

[62] Division of Ser. No. 956,777, filed as PCT/EP91/01254 Jul. 4, 1991.

[30] Foreign Application Priority Data

Jul. 10, 1990 [EP] European Pat. Off. .............. 90201857
Mar. 22, 1991 [EP] European Pat. Off. .............. 91200646

[51] Int. Cl.⁶ .................................................. A61K 31/135
[52] U.S. Cl. ........................................... 514/646; 514/649
[58] Field of Search ....................................... 514/646, 649

[56] References Cited

U.S. PATENT DOCUMENTS 4,246,429  1/1981  Van Daele .............................. 562/456

*Primary Examiner*—José G. Dees
*Assistant Examiner*—Mary C. Cebulak
*Attorney, Agent, or Firm*—Charles J. Metz

[57] ABSTRACT

A compound for use as a medicine having the formula

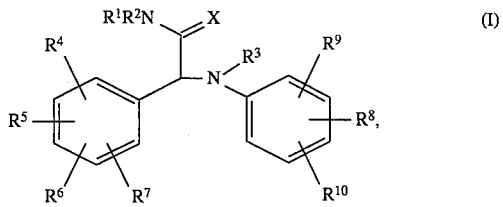

a pharmaceutically acceptable acid addition salt form or a stereochemically isomeric form thereof, wherein $R^1$ and $R^2$ each independently are hydrogen, $C_{1-6}$alkyl or $C_{3-6}$cycloalkyl; or $R^1$ and $R^2$ taken together with the nitrogen atom bearing said $R^1$ and $R^2$ may form a pyrrolidinyl, piperidinyl, morpholinyl, piperazinyl or 4-$C_{1-4}$alkylpiperazinyl group; X is O or S; $R^3$ is hydrogen or $C_{1-6}$alkyl; $R^4$, $R^5$ and $R^6$ each independently are hydrogen, halo, $C_{1-6}$alkyl, $C_{1-6}$alkyloxy, nitro, trifluoromethyl, cyano, aminomethyl, carboxyl, $C_{1-4}$alkyloxycarbonyl, $C_{1-4}$alkyl-carbonyl, aminocarbonyl or hydroxy; $R^7$ is hydrogen or halo; and $R^8$, $R^9$ and $R^{10}$ each independently are hydrogen, halo, $C_{1-6}$alkyl, $C_{1-6}$alkyloxy, nitro, hydroxy, trifluoromethoxy, 2,2,2-trifluoroethoxy, (trifluoromethyl)carbonyl, aminocarbonyl, (cyclopropyl)carbonyl or a radical $C_{1-6}$alkyl-(C=Y)—wherein =Y represents =O, =N—OH, =N—OCH₃, =N—NH₂ or =N—N(CH₃)₂;

provided that (1) $R^1$ is other than n-propyl when $R^2$, $R^3$, $R^4$, $R^5$, $R^6$, $R^7$, $R^9$ and $R^{10}$ represent hydrogen, $R^8$ represents 4-ethoxy and X represents oxygen, and (2) X is other than sulfur, when $R^1$, $R^2$, $R^3$, $R^6$, $R^7$, $R^8$, $R^9$ and $R^{10}$ represent hydrogen and $R^4$ and $R^5$ represent 3,4-dimethoxy.

Novel compounds, pharmaceutical compositions containing said compounds of formula (I), and processes for preparing said compositions.

12 Claims, No Drawings

HIV-INHIBITING BENZENEACETAMIDE DERIVATIVES

CROSS-REFERENCE TO RELATED APPLICATIONS

This application is a divisional of copending application Ser. No. 07/956,777, filed Dec. 17, 1992, which in turn was based upon PCT application PCT/EP 91/01254, filed Jul. 4, 1991, which claimed priority from EP 90.201.857.1, filed Jul. 10, 1990, and EP 91.200.646.7, filed Mar. 22, 1991.

BACKGROUND OF THE INVENTION

In U.S. Pat. No. 4,246,429 corresponding to EP-A-0,006, 713 there are described a number of benzeneacetamides and thioamides being useful as intermediates in the preparation of phytopharmaceutical compounds. Unexpectedly, it has now been found that some of these intermediates effectively inhibit the replication of HIV and consequently may be useful for the treatment of individuals infected by HIV. Moreover, closely related, but hitherto undisclosed compounds were found to inhibit the replication of the retrovirus even better.

Further, in GB-A-1,423,430 there are disclosed benzenethioacetamide compounds, more specifically α-(phenylamino)-3,4-dimethoxybenzenethioacetamide, said compounds having anti-secretory activity.

In Archives Internationales de Pharmacodynamie et de Thérapie, 1966, 164(2), 321–330 there are disclosed alkoxybenzene acetamide derivatives, in particular α-[(4-ethoxyphenyl)amino]-N-propylbenzeneacetamide, said compounds having analgesic properties.

DESCRIPTION OF THE INVENTION

The present invention is concerned with compounds for use as a medicine having the formula

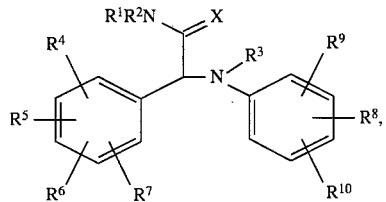

the pharmaceutically acceptable acid addition salt forms and the stereochemically isomeric forms thereof, wherein $R^1$ and $R^2$ each independently are hydrogen, $C_{1-6}$alkyl or $C_{3-6}$cycloalkyl; or $R^1$ and $R^2$ taken together with the nitrogen atom bearing said $R^1$ and $R^2$ may form a pyrrolidinyl, piperidinyl, morpholinyl, piperazinyl or 4-$C_{1-4}$alkylpiperazinyl group;

X is O or S;

$R^3$ is hydrogen or $C_{1-6}$alkyl;

$R^4$, $R^5$ and $R^6$ each independently are hydrogen, halo, $C_{1-6}$alkyl, $C_{1-6}$alkyloxy, nitro, trifluoromethyl, cyano, aminomethyl, carboxyl, $C_{1-4}$alkyloxycarbonyl, $C_{1-4}$alkylcarbonyl, aminocarbonyl or hydroxy;

$R^7$ is hydrogen or halo; and $R^8$, $R^9$ and $R^{10}$ each independently are hydrogen, halo, $C_{1-6}$alkyl, $C_{1-6}$alkyloxy, nitro, hydroxy, trifluoromethoxy, 2,2,2-trifluoroethoxy, (trifluoromethyl)carbonyl, aminocarbonyl, (cyclopropyl)carbonyl or a radical $C_{1-6}$alkyl-(C=Y)—wherein =Y represents =O, =N-OH, =N-OCH$_3$, =N-NH$_2$ or =N-N(CH$_3$)$_2$;

provided that (1) $R^1$ is other than n-propyl when $R^2$, $R^3$, $R^4$, $R^5$, $R^6$, $R^7$, $R^9$ and $R^{10}$ represent hydrogen, $R^8$ represents 4-ethoxy and X represents oxygen, and (2) X is other than sulfur, when $R^1$, $R^2$, $R^3$, $R^6$, $R^7$, $R^8$, $R^9$ and $R^{10}$ represent hydrogen and $R^4$ and $R^5$ represent 3,4-dimethoxy.

The compounds of formula (I) wherein at least one of $R^1$ and $R^2$ is hydrogen may also exist in their tautomeric form. Said form although not explicitly indicated hereinabove is intended to be included within the scope of the present invention.

In the foregoing definitions the term halo defines fluoro, chloro, bromo and iodo; $C_{1-4}$alkyl defines straight and branched saturated hydrocarbon radicals having from 1 to 4 carbon atoms, such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl and the higher homologs thereof having 5 or 6 carbon atoms; $C_{3-6}$cycloalkyl defines cyclopropyl, cyclobutyl, cyclopentyl and cyclohexyl.

Pharmaceutically acceptable addition salts as mentioned hereinabove comprise the therapeutically active non-toxic addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term addition salt also comprises the hydrates and solvent addition forms which the compounds of formula (I) are able to form. Examples of such forms are e.g. hydrates, alcoholates and the like.

Particular compounds are those compounds of formula (I) as defined hereinabove wherein $R^4$, $R^5$ and $R^6$ each independently are hydrogen, halo, $C_{1-6}$alkyl, $C_{1-6}$alkyloxy, nitro or hydroxy;

$R^7$ is hydrogen, $R^8$, $R^9$ and $R^{10}$ each independently are hydrogen, halo, $C_{1-6}$alkyl, $C_{1-6}$alkyloxy, nitro, hydroxy, trifluoromethoxy, 2,2,2-trifluoroethoxy, (trifluoromethyl)carbonyl, aminocarbonyl, (cyclopropyl)carbonyl, or a radical $C_{1-6}$alkyl-C(=Y)—wherein =Y represents =O, =NOH, =NOCH$_3$, or =N—N(CH$_3$)$_2$.

Interesting compounds for use in the method according to the present invention are those compounds of formula (I) wherein $R^1$ and $R^2$ are each independently hydrogen; and/or X is oxygen; and/or $R^4$, $R^5$ and $R^6$ are each independently hydrogen, halo, $C_{1-6}$alkyloxy or nitro; and/or $R^7$ is hydrogen; and/or $R^8$, $R^9$ and $R^{10}$ are each independently hydrogen, halo, $C_{1-6}$alkyl, $C_{1-6}$alkyloxy, nitro, trifluoromethoxy or $C_{1-6}$alkylcarbonyl.

More interesting compounds are those interesting compounds wherein $R^1$ and $R^2$ are each independently hydrogen; and/or $R^3$ is hydrogen; and/or $R^4$, $R^5$ and $R^6$ are each independently hydrogen, halo, methoxy or nitro; and/or $R^8$, $R^9$ and $R^{10}$ are each independently hydrogen, halo, methyl, methoxy, nitro, trifluoromethoxy or methylcarbonyl.

Particularly interesting compounds are those interesting compounds wherein $R^1$ and $R^2$ are hydrogen; $R^4$ represents 2-chloro or 4-methoxy, $R^5$, $R^6$ and $R^7$ being hydrogen; or $R^4$ and $R^5$ represent 2,6-dichloro, 2,4-dichloro or 3,4-dimethoxy, $R^6$ and $R^7$ being hydrogen; or $R^4$, $R^5$ and $R^6$ represent 2,6-dichloro-3-nitro or 2,3,6-trichloro; $R^7$ being hydrogen; or $R^4$, $R^5$, $R^6$ and $R^7$ represent 2,3,6-trichloro-4-trifluoromethyl; and/or $R^8$ represents hydrogen, chloro, methyl, methoxy, nitro, trifluoromethoxy or methylcarbonyl, $R^9$ and $R^{10}$ being hydrogen; or $R^8$ and $R^9$ represent 2,4-dimethyl, 2,5-dimethyl, 2,4-dichloro, 2,6-dichloro, 3,5-dichloro, 2-hydroxy-5-chloro, 2-methoxy-5-chloro, 2-nitro-5-chloro, 2-nitro-5-methyl, 2-methoxy-5-methyl, 2-methylcarbonyl-5-methyl, 2-methylcarbonyl-5-chloro, 2-methylcarbonyl-5-fluoro or 2-chloro-4-nitro, $R^{10}$ being hydrogen.

The most interesting compounds within the present invention are those wherein $R^4$ and $R^5$ represent 2,6-dichloro, $R^6$ and $R^7$ being hydrogen; or $R^4$, $R^5$ and $R^6$ represent 2,3,6-trichloro; $R^7$ being hydrogen; $R^8$ represents 2-methoxy, 2-nitro, 2-methylcarbonyl, 2-trifluoro-methoxy, 3-methyl, $R^9$ and $R^{10}$ being hydrogen; or $R^8$ and $R^9$ represent 2-methoxy-5-methyl, 2-nitro-5-chloro, 2-nitro-5-methyl, 2-methoxy-5-chloro, 2-methylcarbonyl-5-methyl, 2-methylcarbonyl-5-fluoro or 2-methylcarbonyl-5-chloro, $R^{10}$ being hydrogen.

Preferred compounds are (−)-α-[(2-nitrophenyl)amino]-2,6-dichlorobenzeneacetamide, (−)-α-[(5-methyl-2-nitrophenyl)amino]-2,6-dichlorobenzeneacetamide, (−)-α-[(2-acetylphenyl)amino]-2,6-dichlorobenzeneacetamide, (−)-α-[(2-acetyl-5-methylphenyl)amino]-2,6-dichlorobenzeneacetamide, α-[(2-acetyl-5-chlorophenyl)amino]-2,6-dichlorobenzeneacetamide, α-[(5-chloro-2-nitrophenyl)amino]-2,6-dichlorobenzeneacetamide, and α-[(2-acetyl-5-fluorophenyl)amino]-2,6-dichlorobenzeneacetamide.

An additional feature of the present invention comprises the fact that a number of the compounds of formula (I) are deemed novel and have especially been developed for use in the method according to the present invention.

An interesting subgroup of novel compounds is formed by the compounds of formula

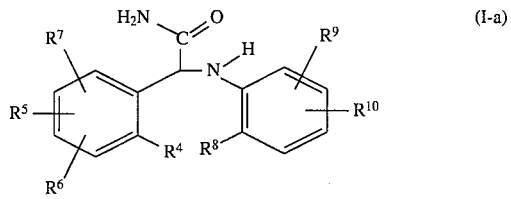

the pharmaceutically acceptable acid addition salt forms and the stereochemically isomeric forms thereof, wherein $R^4$ represents halo, $C_{1-6}$alkyl, $C_{1-6}$alkyoxy or nitro;

$R^5$ and $R^6$ each independently represent hydrogen, halo, $C_{1-6}$alkyl, $C_{1-6}$alkyloxy, nitro, trifluoromethyl, cyano, aminomethyl, carboxyl, $C_{1-4}$alkyloxycarbonyl, $C_{1-4}$alkylcarbonyl, aminocarbonyl or hydroxy; $R^7$ represents hydrogen or halo;

$R^8$ represents $C_{1-6}$alkyloxy, nitro, trifluoromethoxy, 2,2,2-trifluoroethoxy, (trifluoromethyl)carbonyl, aminocarbonyl, (cyclopropyl)carbonyl or a radical $C_{1-6}$alkyl-(C=Y)— wherein =Y represents =O, =N—OH, =N—OCH$_3$, =N—NH$_2$ or =N—N(CH$_3$)$_2$, and $R^9$ and $R^{10}$ each independently are hydrogen, halo, $C_{1-6}$alkyl, $C_{1-6}$alkyloxy, nitro, hydroxy, trifluoromethoxy, 2,2,2-trifluoroethoxy, (trifluoromethyl)carbonyl, aminocarbonyl, (cyclopropyl)carbonyl or a radical $C_{1-6}$alkyl-(C=Y)— wherein =Y represents =O, =N—OH, =N—OCH$_3$, =N—NH$_2$ or =N—N(CH$_3$)$_2$;

provided that $R^8$ is other than 2-methoxy when $R^4$ is chloro, $R^5$ is 6-chloro, $R^6$, $R^7$ and $R^9$ are hydrogen and $R^{10}$ is hydrogen or 5-methyl.

An interesting subgroup of novel compounds is formed by the compounds of formula (I) or of formula (I-a) wherein the asymmetric carbon atom bearing the amide group has the same absolute configuration as in (−)-α-[(2-nitrophenyl)amino]-2,6-dichlorobenzeneacetamide.

Another subgroup of novel compounds is formed by the compounds of formula (I) or of formula (I-a) wherein the asymmetric carbon atom bearing the amide group has the reversed absolute configuration as in (−)-α-[(2-nitrophenyl)amino]-2,6-dichlorobenzeneacetamide.

Novel compounds of particular interest are those novel compounds wherein $R^4$ is halo or $C_{1-6}$alkyl; $R^5$ and $R^6$ are hydrogen, halo or $C_{1-6}$alkyl; $R^7$ is hydrogen or chloro; $R^8$ is $C_{1-6}$alkyloxy, trifluoromethoxy, nitro or $C_{1-6}$alkylcarbonyl; $R^9$ and $R^{10}$ are hydrogen, halo or $C_{1-6}$alkyl.

The most interesting novel compounds are those wherein $R^4$ is chloro or methyl; $R^5$ is hydrogen, chloro or methyl; $R^6$ is hydrogen or chloro; $R^7$ is hydrogen, $R^8$ is methoxy, trifluoromethoxy, nitro or methylcarbonyl; $R^9$ is hydrogen, chloro, fluoro or methyl; and $R^{10}$ is hydrogen.

Preferred novel compounds are those wherein $R^4$ is chloro; $R^5$ is 6-chloro or 6-methyl; $R^6$ is hydrogen or 3-chloro; $R^7$ is hydrogen; $R^8$ is methoxy, trifluoromethoxy, nitro or methylcarbonyl; $R^9$ is hydrogen, 5-chloro, 5-fluoro or 5-methyl; and $R^{10}$ is hydrogen.

The most preferred novel compounds are (−)-α-[(2-nitrophenyl)amino]-2,6-dichlorobenzeneacetamide, (−)-α-[(5-methyl-2-nitrophenyl)amino]-2,6-dichlorobenzeneacetamide, (−)-α-[(2-acetylphenyl)amino]-2,6-dichlorobenzeneacetamide, (−)-α-[(2-acetyl-5-methylphenyl)amino]-2,6-dichlorobenzeneacetamide, α-[(2-acetyl-5-chlorophenyl)amino]-2,6-dichlorobenzeneacetamide, α-[(5-chloro-2-nitrophenyl)amino]-2,6-dichlorobenzeneacetamide, and α-[(2-acetyl-5-fluorophenyl)amino]-2,6-dichlorobenzeneacetamide.

The compounds of formula (I) and the compounds of formula (I-a) can generally be prepared following art-known procedures such as, for example, the procedures described in U.S. Pat. No. 4,246,429 and alternative procedures known in the art. The most interesting processes are described hereinbelow in more detail for the compounds of formula (I). Obviously, similar process for the preparation of the novel compounds of formula (I-a) are intended to be included thereby.

The compounds of formula (I) can generally be prepared by alkylating an appropriate aniline derivative of formula (II) or a salt thereof, with an alkylating reagent of formula (III) following art-known N-alkylation procedures.

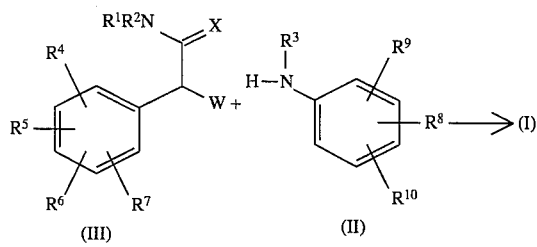

In formula (III) and hereinafter W represents a reactive leaving group such as, for example, halo, e.g. chloro, bromo or iodo, a sulfonyloxygroup, e.g. methanesulfonyloxy, trifluoromethanesulfonyloxy, benzenesulfonyloxy, 4-methylbenzenesulfonyloxy, naphthalenesulfonyloxy and the like reactive leaving groups. In formula (II), $R^3$ represents hydrogen or $C_{1-6}$alkyl and may also represent formyl (—CHO). Said formyl derivatives are particularly useful for preparing salt forms of the intermediates of formula (II). In the subsequently obtained formylated end-products of formula (I) the formyl group may be replaced by hydrogen by hydrolysis or alternatively may be reduced to methyl following conventional reduction procedures.

Said N-alkylation reaction can conveniently be carried out by stirring the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, an amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. Usually, it is advantageous to convert the formylated intermediate of formula (II) first into a suitable salt form thereof such as, for example, an alkali, earth alkaline metal salt, by reacting (II) with an appropriate base as defined hereinabove, and subsequently using said salt form in the reaction with the alkylating reagent of formula (III). Said alkali, earth alkaline metal can be for example, sodium, potassium, lithium, calcium, and the like. In some instances the addition of a iodide salt, preferably an alkali metal iodide, or a crown ether, e.g. 1,4,7,10,13,16-hexaoxacyclooctadecane and the like, may be appropriate. Stirring and elevated temperatures enhance the rate of the reaction; more in particular the reaction may be conducted at the reflux temperature of the reaction mixture. Additionally, it may be advantageous to conduct said alkylation under an inert atmosphere such as, for example, oxygen-free argon or nitrogen gas.

Alternatively, said alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Elevated temperatures may be appropriate to enhance the rate of the reaction.

An efficient alternative for the foregoing N-alkylation reactions comprises heating an intermediate of formula (III) in an excess of the aniline derivative of formula (II) in the absence of any solvent. The reaction is conducted by stirring and heating the mixture to a temperature effecting complete dissolution of the reagents.

In all of the foregoing and in the following preparations, the reaction products may be isolated from the reaction mixture and, if necessary, further purified according to methodologies generally known in the art.

The compounds of formula (I) wherein $R^1$ and $R^2$ are hydrogen, said compounds being represented by formula (I-b) when X is O and by formula (I-c) when X is S, can be prepared by reacting a nitrile of formula (IV) with a reagent $H_2X$ (V), namely water or hydrogen sulfide, under appropriate conditions.

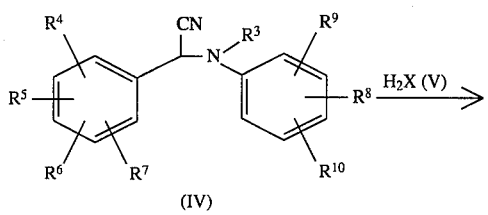

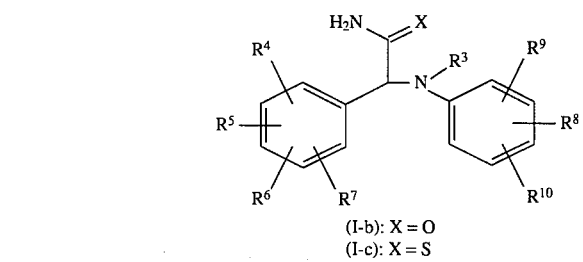

The hydrolysis of the nitrile (IV) to the corresponding amide (I-b) wherein X is O, can easily be carried out following art-known procedures. Preferably said hydrolysis is carried out at room temperature in a concentrated strong acid, e.g. concentrated sulfuric acid, hydrochloric acid, hydrobromic acid, formic acid saturated with hydrochloric acid and the like, optionally in the presence of a small amount of water.

The nitrile (IV) can conveniently be converted into the thioamide (I-c) wherein X is S by reaction with hydrogen sulfide in an appropriate solvent, e.g. pyridine, a mono-, di- or trimethylated pyridine and the like solvents, and in the presence of an appropriate base such as an amine, e.g. N,N-diethylethanamine, 1-methylmorpholine, N-(1-methylethyl)-1-methylethanamine and the like. This latter reaction can conveniently be conducted at room temperature and in some instances even at lower temperatures such as, for example, between about 0° C. and room temperature. The thioamide compounds of formula (I-c) can conveniently be converted into the corresponding amides of formula (I-b) by reaction with an oxidizing reagent such as, for example, hydrogen peroxide in water, optionally in admixture with a reaction-inert organic co-solvent.

The compounds of formula (I) wherein X is O and at least one and possibly several of $R^8$, $R^9$ and $R^{10}$ represent electron-withdrawing groups such as, for example, halo, nitro or $C_{1-6}$alkyloxy, said compounds being represented by formula (I-d) may be prepared by N-arylating an intermediate of formula (VI) with an appropriate benzene derivative of formula (VII).

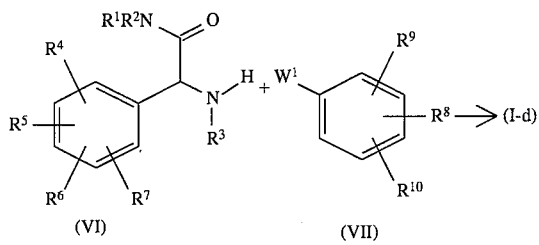

In formula (VII) $W^1$ represents a reactive leaving group, such as, for example, halo, $C_{1-6}$alkyloxy, aryloxy, ($C_{1-6}$alkyl or aryl)sulfonyloxy, ($C_{1-6}$alkyl or aryl)sulfonyl, $C_{1-6}$alkylthio or nitro, preferably fluoro, chloro, nitro, 4-methylbenzenesulfonyloxy, methoxy or methylthio. Said arylation reaction can conveniently be carried out following the procedures described hereinbefore for the alkylation reaction of intermediate (II) with intermediate (III). More in particular, the reactants may be stirred, preferably at a somewhat elevated temperature and in particular at the reflux temperature, in the presence of a base as defined in the above-mentioned alkylation reaction, in an appropriate solvent such as, for example, a dipolar aprotic solvent, e.g. N,N-dimethylformamide, N,N-dimethylacetamide, dimethylsulfoxide, 1-methyl-2-pyrrolidinone, acetonitrile, pyridine, hexamethylphosphor triamide; an alcohol, e.g. 1-butanol; an ether, e.g. tetrahydrofuran, 1,1'-oxybisethane, 1,4-dioxane and the like; and mixtures of such solvents. Phase transfer catalysis conditions may equally well be employed in the above arylation reaction.

Further, the compounds of formula (I) wherein X is O, said compounds being represented by formula (I-e), may also be obtained by amidation of the corresponding carboxylic acids or suitable reactive functional derivatives thereof, of formula (VIII). In (VIII) L may represent hydroxy, $C_{1-6}$alkyloxy, phenoxy (optionally further substituted), 1H-imidazolyl, ($C_{1-6}$alkyl or phenyl)oxycarbonyloxy, halo, and the like reactive leaving groups.

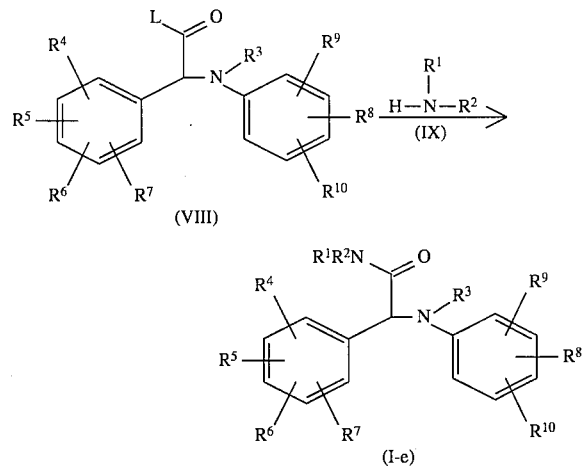

Said preparation of the amides of formula (I-e) can conveniently be carried out following art-known amidation and transamidation reactions. For example, said amides can be prepared by reacting an appropriate carboxylic acid (L is OH) with an amine (IX) in the presence of a reagent capable of promoting amidation reactions. Typical examples of such reagents are for example, dicyclohexylcarbodiimide, 2-chloro-1-methylpyridinium iodide, phosphorus pentoxide, 1,1'-carbonylbis[1H-imidazole], 1,1'-sulfonylbis[1H-imidazole] and the like reagents.

Alternatively, said carboxylic acids may be converted into a suitable reactive functional derivative thereof such as, for example, an acyl halide, symmetric or mixed anhydride, ester, amide, acyl azide and the like derivatives, before reaction with the amine $HNR^1R^2$. Said reactive functional derivatives may be prepared following art known methods, for example, by reacting the carboxylic acid with a halogenating reagent such as, for example, thionyl chloride, phosphorous trichloride, polyphosphorous acid, phosphoryl chloride, oxalyl chloride and the like, or by reacting said carboxylic acid with an acyl halide such as acetyl chloride, ethyl chloroformate and the like. A particularly interesting method for preparing the amides wherein $R^3$ is hydrogen comprises reacting a suitable carboxylic acid derivative with a carbonate forming reagent such as, for example, carbonoic dichloride, trichloromethyl chloroformate, 1,1'-carbonylbis [1H-imidazole], di($C_{1-6}$alkyl)carbonate and the like, thus yielding a cyclic anhydride of formula (VIII-a), and subsequently reacting said cyclic anhydride with the amine $R^1R^2NH$.

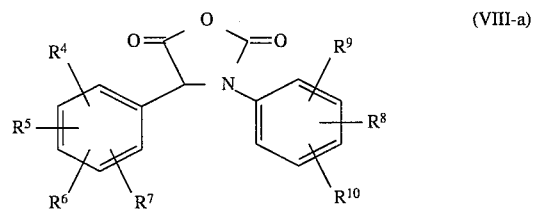

Said reactive functional derivatives of the carboxylic acids may be generated in situ, or if desired, be isolated and further purified before reacting them with the amine $HNR^1R^2$. Amidation of said reactive functional derivatives can conveniently be carried out by stirring the reactants, optionally in a suitable reaction-inert solvent such as, for example, a halogenated hydrocarbon, e.g. dichloromethane, trichloromethane and the like; an aromatic hydrocarbon, e.g. benzene, methylbenzene and the like; an ether, e.g. 1,1'-oxybisethane, tetrahydrofuran and the like; or a dipolar aprotic solvent, e.g. N,N-dimethylformamide, N,N-dimethylacetamide, pyridine and the like. In some instances it may be appropriate to employ an excess of one of the reagents as solvent. The water, acid, alcohol or amine which may be liberated during the course of the reaction can be removed from the reaction mixture by art-known procedures such as, for example, azeotropical distillation, complexation, salt formation and the like methods. In some instances particularly the addition of a suitable base such as, for example, an amine, e.g. N,N-diethylethanamine, 4-ethylmorpholine, pyridine or N,N-dimethyl-4-pyridinamine, may be appropriate. Further, in order to enhance the rate of the reaction, said amidation reaction may advantageously be conducted at a somewhat elevated temperature, in particular the reflux temperature of the reaction mixture.

The compounds of formula (I) can also be converted into one another following art-known functional group transformation reactions. For example, the compounds wherein one of $R^8$, $R^9$ or $R^{10}$ represents a radical $C_{1-6}$alkyl-C(=Y)— wherein Y represents =N—OH, =N—OCH$_3$, =N—NH$_2$ or =N—N(CH$_3$)$_2$, can be prepared following art-known procedures from the corresponding compounds wherein Y represents =O by reaction with hydroxylamine, O-methylhydroxylamine, hydrazine or di(methyl)hydrazine or a suitable addition salt form thereof.

The compounds of this invention have at least one asymmetric carbon atom in their structure, namely the carbon atom bearing the amide or thioamide group. Said chiral center and any other chiral center which may be present, can be indicated by the stereochemical descriptors R and S.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like; and enantiomers may be separated from each other following art-known resolution methods, for example, by the selective crystallization of their diastereomeric salts with chiral. acids. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I) as prepared in the above described processes are generally racemic mixtures of enantiomers which can be separated from one another following art-known resolution procedures. The racemic compounds of formula (I) which are sufficiently basic may be converted into the corresponding diastereomeric salt forms by reaction with a suitable chiral acid. Said diastereomeric salt forms are subsequently separated, for example, by selective or fractional crystallization and the enantiomers are liberated therefrom by alkaline or acidic hydrolysis.

A preferred manner of separating the enantiomeric forms of the compounds of formula (I) involves liquid chromatography using a chiral stationary phase such as suitably derivatized cellulose, for example, tri(dimethylcarbamoyl)cellulose (Chiracel OD®) and similar chiral stationary phases.

As an alternative to the above-mentioned resolution of the compounds of formula (I), there should be mentioned also the resolution of racemic intermediates. Particularly useful intermediates for this purpose are the aminoacids of formula

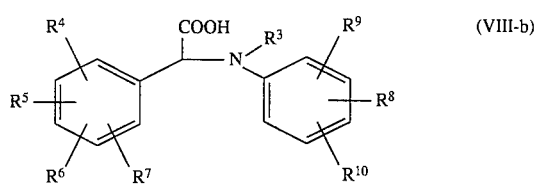

which can easily be obtained from the corresponding benzene(thio)acetamide compounds of formula (I) by acidic or, preferably, alkaline hydrolysis, for example, by treatment with an aqueous solution of a base such as sodium or potassium hydroxide, in admixture with a suitable organic solvent such as, for example, an alkanol, e.g. methanol, ethanol and the like. The thus obtained aminoacids of formula (VIII-b) can conveniently be resolved by formation of the corresponding diastereomeric salt forms by reaction with a suitable chiral base such as phenylethanamine, naphthylethanamine, cinchonine and other alkaloid bases. Obviously, said aminoacids may also be resolved by liquid chromatography using an appropriate chiral stationary phase.

The enantiomeric forms of the aminoacids of formula (VIII-b) are converted into the enantiomeric forms of the benzene(thio)acetamide compounds of formula (I) according to the procedures described hereinbefore for converting the intermediates of formula (VIII) into the compounds of formula (I).

Other interesting, novel intermediates or derivatives of the racemic compounds of formula (I) for resolution by liquid chromatography are, for example, the iminoethers of formula (VIII-c) and the derivatives of formula (VIII-d)

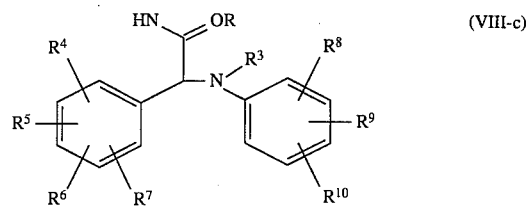

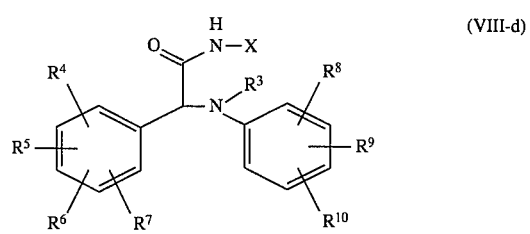

Some of the intermediates of formula (VIII-c) and (VIII-d) are particularly interesting due to their relatively greater solubility thus allowing one to load more racemic material on the chiral stationary phase. The intermediates of formula (VIII-c) can be prepared from the nitriles of formula (IV) by alcoholysis with an alcohol ROH wherein R represents $C_{1-6}$alkyl or phenyl, in the presence of dry hydrochloric acid. After resolution by liquid chromatography, the separated enantiomers of formula (VIII-c) are converted into the corresponding enantiomeric amides of formula (I-b), by hydrolysis of the iminoether in an aqueous acidic medium to the carboxylic acid and further conversion as described hereinabove.

In the intermediates of formula (VIII-d) X represents a radical of formula —$CH_2OH$ or —$CH_2N(CH_3)$. Said intermediates can easily be prepared from the amides of formula (I-b) by reaction with formaldehyde or [$(CH_3)_2N=CH_2$]$^+$ Cl$^-$ following art-known procedures. Thermolysis of the separated enantiomers yields the corresponding enantiomeric amides of formula (I-b).

A number of the intermediates and starting materials employed in the foregoing preparations are known compounds which can be prepared according to art-known methodologies of preparing said or similar compounds. Some intermediates are less common or are novel, and a number of preparation methods will therefore be described hereinafter in more detail.

The intermediates (III) wherein X is O, may be obtained from α-hydroxy benzeneacetic acid derivatives of formula (X) by reaction with a halogenating reagent such as, for example, phosphorus pentachloride, phosphoryl chloride, phosphorous trichloride, phosphorous tribromide, thionyl chloride and the like, or another activating reagent such as, for example, a sulfonylhalide. Said reaction can be conducted at an elevated temperature, in particular the reflux temperature of the reaction mixture, in an excess of the halogenating reagent as solvent, which may optionally be diluted with a suitable reaction-inert solvent such as an aromatic hydrocarbon, a halogenated hydrocarbon, an ether and the like solvents. The thus obtained benzeneacetyl halide is conveniently converted into the desired benzeneacetamide by pouring the reaction mixture into an aqueous or alcoholic solution comprising an amine of formula HNR¹R² (IX).

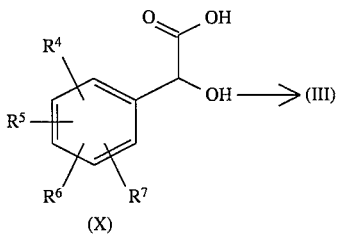

The intermediates of formula (IV-a) can be prepared by reacting an appropriate benzaldehyde (XII) with an aniline of formula (XI) in the presence of a cyanide salt and a suitable solvent.

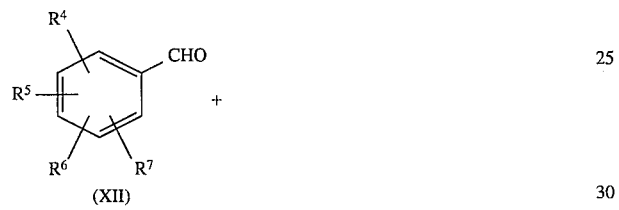

As examples of cyanide salts there may be mentioned alkali metal and earth alkaline metal cyanides, e.g., sodium and potassium cyanide. Suitable solvents comprise, for example, water, alkanols, e.g. methanol, ethanol and the like, carboxylic acids, e.g. acetic acid, particularly glacial acetic acid, propanoic acid and the like; or a mixture of such solvents. Said reaction is conveniently carried out by stirring at room temperature and, if desired, slightly heating the reactant, for example between 40° C. and 60° C., in particular at about 50° C. In some instances it is advantageous to carry out said reaction in the presence of a metal salt such as, for example, anhydrous zinc chloride and the like, in a non-aqueous solvent, particularly glacial acetic acid, as described in Chem. Ber., 98, 3902 (1965).

Alternatively, the intermediates of formula (IV-a) can also be prepared by converting a N-arylbenzamide (XIII) into an imidoyl chloride (XIII-a) with a halogenating reagent, reacting said imidoyl halide with a cyanide salt and reducing the thus obtained α-iminonitrile (XIII-b).

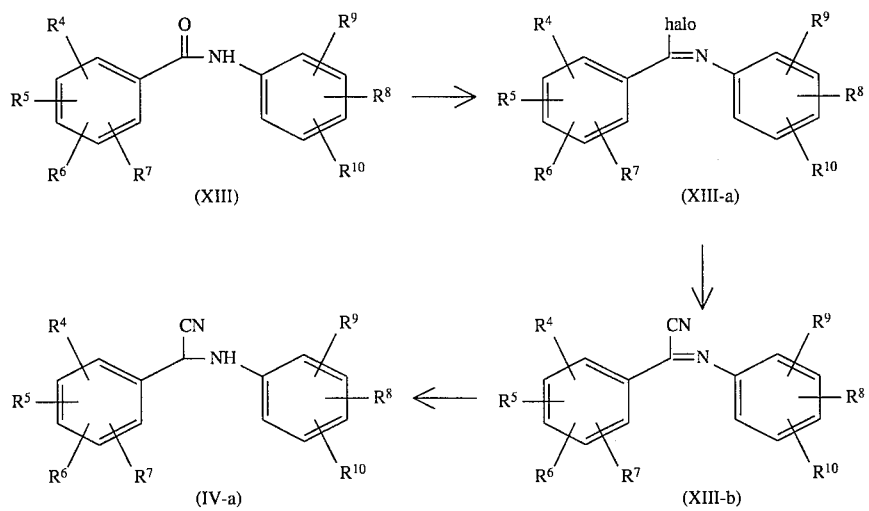

-continued

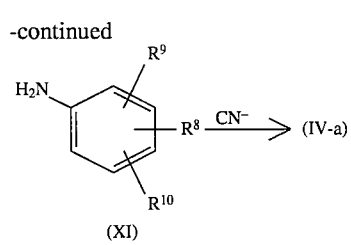

Said imidoyl halide can be prepared by reacting (XIII) with a halogenating reagent such as, for example, phosphorus pentachloride, phosphoryl chloride, phosphorous trichloride, phosphorous tribromide, thionyl chloride and the like, in a suitable solvent, such as for example, a halogenated hydrocarbon, e.g. dichloromethane, trichloromethane; an ether, e.g. tetrahydrofuran, 1,1'-oxybisethane, 1,4-dioxane and the like; or a mixture of such solvents; or in an excess of the halogenating reagent, optionally in admixture with one or more of the cited solvents.

The substitution reaction of halo by cyano can be carried out in a reaction-inert solvent with a cyanide salt such as described hereinabove in the preparation of (IV-a) from the aldehyde (XII). Preferably said substitution is carried out under phase-transfer catalysis conditions in a two-phase solvent system as described in Synthesis 1978, p. 894. The thus obtained intermediate (XIII-b) then is reduced to (IV-a) in the presence of an appropriate reducing agent such as, for example, sodium borohydride, lithium borohydride, sodium cyanoborohydride, lithium aluminum hydride and the like reducing agents.

A number of the intermediates of formula (IV) are deemed novel. An interesting subgroup of novel intermediates of formula (IV) is formed by the intermediates of formula

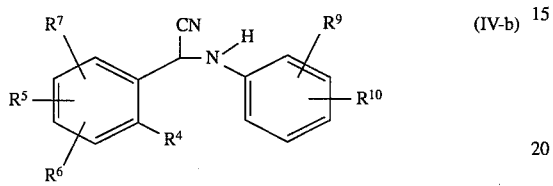

(IV-b)

and the stereochemically isomeric form thereof, wherein $R^4$ represents halo, $C_{1-6}$alkyl, $C_{1-6}$alkyloxy, nitro or hydroxy;

$R^5$ and $R^6$ each independently represent hydrogen, halo, $C_{1-6}$alkyl, $C_{1-6}$alkyloxy, nitro, trifluoromethyl, cyano, aminomethyl, carboxyl, $C_{1-4}$alkyloxycarbonyl, $C_{1-4}$alkylcarbonyl, aminocarbonyl or hydroxy: $R^7$ represents hydrogen or halo;

$R^8$ represents $C_{1-6}$alkyloxy, nitro, trifluoromethyloxy, 2,2,2-trifluoroethoxy, (trifluoromethyl)carbonyl, aminocarbonyl,(cyclopropyl)carbonyl or a radical $C_{1-6}$alkyl-(C=Y)—wherein =Y represents =O, =N—OH, =N—OCH$_3$, =N—NH$_2$ or =N—N(CH$_3$)$_2$, and $R^9$ and $R^{10}$ each independently are hydrogen, halo, $C_{1-6}$alkyl, $C_{1-6}$alkyloxy, nitro, hydroxy, trifluoromethoxy, 2,2,2-trifluoroethoxy, (trifluoromethyl)carbonyl, aminocarbonyl, (cyclopropyl)carbonyl or a radical $C_{1-6}$alkyl-(C=Y)—wherein =Y represents =O, =N—OH, =N—OCH$_3$, =N—NH$_2$ or =N—N(CH$_3$)$_2$;

provided that $R^8$ is other than 2-methoxy when $R^4$ is chloro, $R^5$ is 6-chloro, $R^6$, $R^7$ and $R^9$ are hydrogen and $R^{10}$ is hydrogen or 5-methyl.

The intermediates of formula (VI) can conveniently be prepared from a suitable carboxylic acid derivative wherein L is as defined in (VIII) by reaction with an amine HNR$^1$R$^2$ (LX).

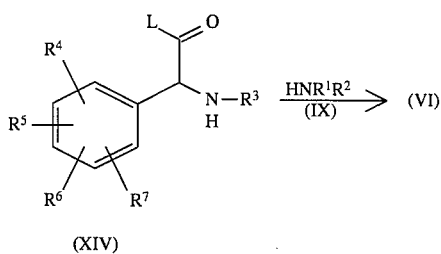

(XIV)

Alternatively, the intermediates (VI) wherein $R^1$ and $R^2$ are hydrogen can be prepared by hydrolysis of an intermediate (XV) following the procedures described hereinbefore for the preparation of compound (I-b).

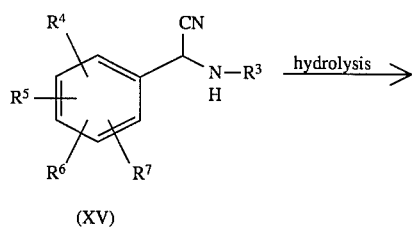

(XV)

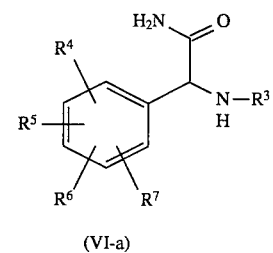

(VI-a)

An alternative method for converting the intermediates of formula (XV) into the intermediates of formula (VI-a) comprises stirring the intermediate of formula (XV) in an alkanol such as methanol, in the presence of a ketone such as acetone or cyclohexanone (R(C=O)—R) and a catalytical amount of a base such as sodium methoxide and the like. The thus obtained cyclic intermediate (XVI), which may rearrange to an intermediate of formula (XVII) is then hydrolysed to an intermediate of formula (VI-a) by heating in water.

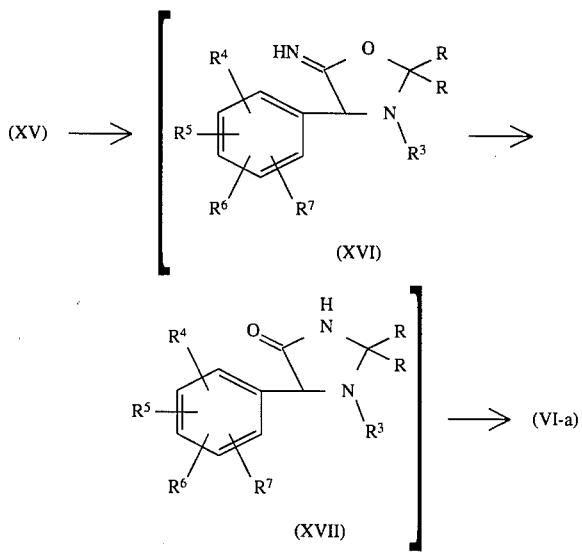

Obviously, the intermediates of formula (XV) can easily be obtained from benzaldehydes of formula (XII) by reaction with an appropriate amine $R^3$—NH$_2$ and cyanide as described hereinbefore for the preparation of the intermediates (IV-a).

A number of the anilines of formula (XI) are novel and have especially been prepared for use in the present invention. For example, the intermediates of formula (XI-a) wherein $R^8$ represents $C_{1-6}$alkyl-C(=O)—can be prepared from a nitrile (XVIII-a) or carboxylic acid of formula (XVIII-b),

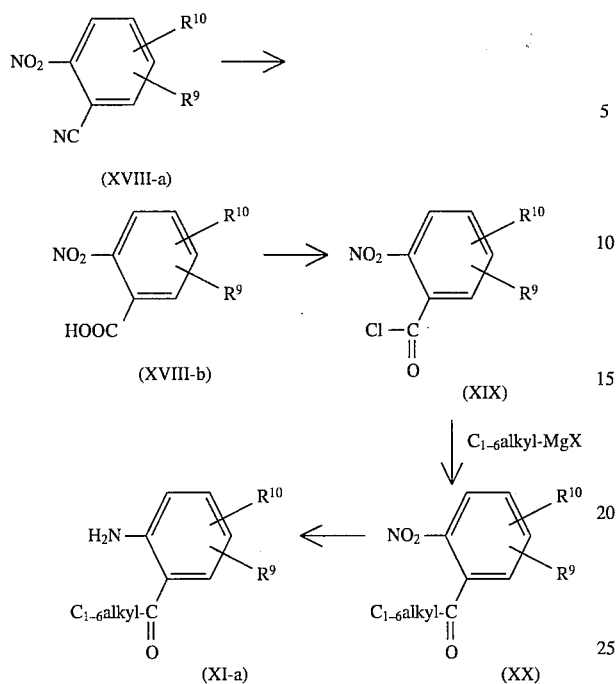

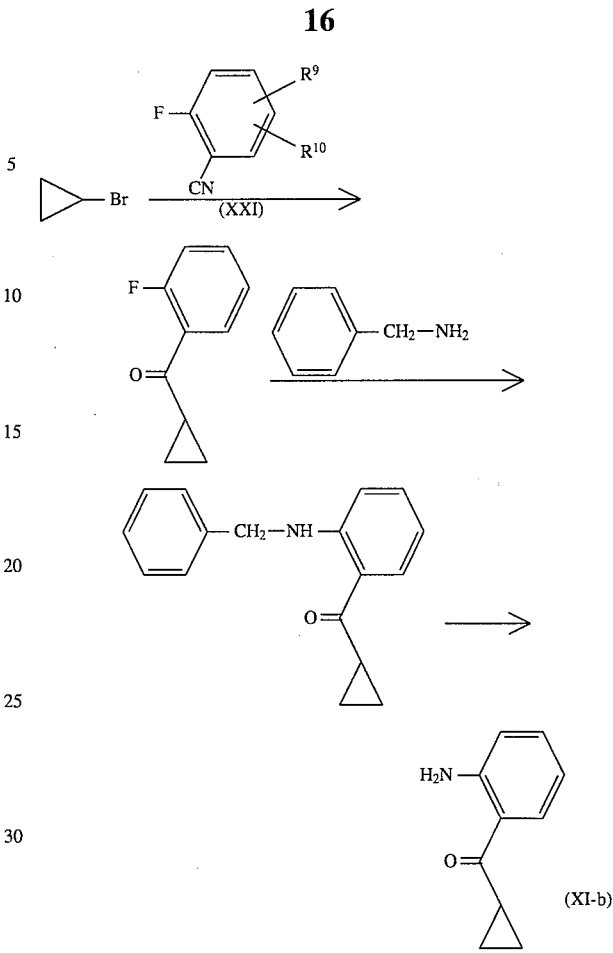

via the acyl chloride (XIX) which is reacted with an organometallic reagent such as $C_{1-6}$alkyl magnesium halide or a dialkyl-2-$C_{1-6}$alkyl-1,3-propanedioate magnesium salt. The latter yields a malonic ester derivative which is converted into (XX) by acid hydrolysis and concomitant decarboxylation. Reduction of the nitro group yields intermediate (XI-a).

Intermediates of formula (XI-b) wherein $R^8$ represents (cyclopropyl)carbonyl can be prepared from a 2-fluorobenzenenitirile (XXI) by reaction with the Grignard reagent derived from cyclopropane bromide, followed by nucleophilic aromatic substitution of fluoro and hydrogenolysis of the benzyl group.

The aldehydes of formula (XII) can generally be prepared from the corresponding toluene derivatives (XXII) by bromination, hydrolysis and oxidation.

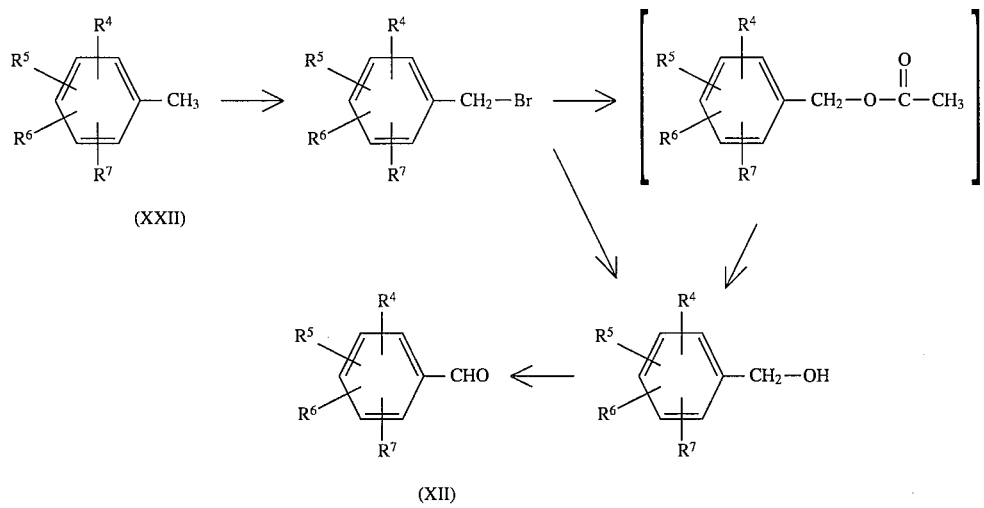

The compounds of formula (I) show antiretroviral properties, in particular against Human Immunodeficiency Virus (HIV), also known as LAV, HTLV-III or ARV, which is the etiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

Due to their antiretroviral properties, especially their anti-HIV properties, the compounds of formula (I), their pharmaceutically acceptable salts and the stereochemically isomeric forms thereof, are useful in the treatment of individuals infected by HIV and for the prophylaxis of individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

Additionaly, it has been found that also the intermediates of formula (IV) show antiretroviral properties, in particular against HIV.

In view of their pharmacological properties, the subject compounds may be formulated into various pharmaceutical forms for administration purposes. Said pharmaceutical forms or compositions are deemed novel and consequently constitute another aspect of the present invention. Also the preparation of said compositions constitutes a further aspect of the present invention. To prepare the pharmaceutical compositions of this invention, an effective amount of the active ingredient is combined in intimate admixture with a pharmaceutically acceptable carrier. These pharmaceutical compositions are desirably in unitary dosage form suitable, for administration orally, rectally, percutaneously, or by parenteral injection. For example, in preparing the compositions in oral dosage form, any of the usual pharmaceutical media may be employed, such as, for example, water, glycols, oils, alcohols and the like, in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their case in administration, tablets and capsules represent the most advantageous oral dosage unit form. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

The present invention is also related with a method of treating viral diseases in warm-blooded animals suffering from said viral diseases by administering an effective antiviral amount of a compound of formula (I), a pharmaceutically acceptable acid addition salt or a stereoisomeric form thereof. Those of skill in the treatment of HIV-infection could easily determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention. Unless otherwise stated all parts therein are by weight.

EXPERIMENTAL PART

A. Preparation of the intermediates

EXAMPLE 1

To a stirred mixture of 43.8 parts of 2,6-dichlorobenzaldehyde and 325 parts of acetic acid there were added dropwise 35.3 parts of 2-methoxybenzamine. After 15 min, there was added dropwise a solution of 20.3 parts of potassium cyanide in 35 parts of water, keeping the temperature below 30° C. Stirring was continued for 20 hours at room temperature. The precipitate was filtered off and recrystallized from 2-propanol (2×). The product was filtered off and dried, yielding 35.3 parts of 2-(2,6-dichlorophenyl)-2-[(2-methoxyphenyl)amino]acetonitrile; mp. 117.5° C. (interm. 1).

EXAMPLE 2

To a stirred and cooled (ice-bath) mixture of 44 parts of 2,6-dichlorobenzaldehyde and 500 parts of acetic acid there were added 27.6 parts of 2-nitrobenzamine, 50 parts of zinc(II)chloride and 16.3 parts of potassium cyanide. Stirring was continued for 17 hours at 50° C. After cooling, the reaction mixture was poured into 1000 parts of water. The precipitate was filtered off and triturated with 2,2'-oxybispropane. The product was filtered off, washed with 2,2'-oxybispropane and dried, yielding 45.9 parts of 2-(2,6-dichlorophenyl)-2-[(2-nitrophenyl)amino]acetonitrile; mp. 194.8° C. (interm. 2).

EXAMPLE 3

A mixture of 8.75 parts of 2,6-dichlorobenzaldehyde, 5.4 parts of 1-(2-aminophenyl)-1-ethanone and 105 parts of acetic acid was stirred for ½ hour at room temperature. There were added 3.26 parts of potassium cyanide and stirring was continued for 20 hours. The reaction mixture was diluted with water. The precipitate was filtered off, washed with water and recrystallized from acetonitrile. The product was filtered off and dried, yielding 9.1 parts (71.3%) of (±)-α-[(2-acetylphenyl)amino]-2,6-dichlorobenzeneacetonitrile; mp. 178.7° C. (interm. 3).

EXAMPLE 4 a) A mixture of 2 parts of 4-ethyl-2-nitrobenzenecarbonitrile, 31.6 parts of ethanol, 27.8 parts of hydrogen peroxide (30%) and 1.7 ml of sodium hydroxide 6N was stirred for 1 hour at room temperature. The reaction mixture was diluted with water and the product was extracted with dichloromethane (3×). The combined extracts were washed with water, dried, filtered and evaporated. The residue was crystallized from 2,2'-oxybispropane. The product was filtered off and dried, yielding 1.3 parts (60.9%) of 4-ethyl-2-nitrobenzamide; mp. 175.0° C. (interm. 4).

b) To a stirred and heated (80° C.) mixture of 29.2 parts of intermediate 4 and 234 parts of sulfuric acid (75%) there were added portionwise 53 parts of sodium nitrite. The whole was stirred at room temperature for 10 min and was then diluted with water. The precipitate was filtered off, washed with water and dried, yielding 26 parts (88.8%) of 4-ethyl-2-nitrobenzoic acid; mp. 111.2° C. (interm. 5).

c) A mixture of 25.5 parts of intermediate 5 and 259.2 parts of thionyl chloride was stirred for 5 hours at reflux temperature. The reaction mixture was evaporated and the residue was co-evaporated with methylbenzene (2×), yielding 27.8 parts (100%) of 4-ethyl-2-nitrobenzenecarbonyl chloride (interm. 6).

d) To a stirred mixture of 3.4 parts of magnesium turnings, 2.0 parts of ethanol and 2.2 parts of tetrachloromethane there were added dropwise 35.5 parts of 1,1'-oxybisethane. At reflux temperature, there were added dropwise a mixture of 22.4 parts of diethyl 1,3-propanedioate, 11.9 parts of ethanol and 10.7 parts of 1,1'-oxybisethane and, after 3 hours, a solution of 27.8 parts of intermediate 6 in 10.7 parts of 1,1'-oxybisethane. Stirring at reflux temperature was continued for 1 hour. After cooling, there were added dropwise 91.4 parts of $H_2SO_4$ (8%). The organic layer was separated and the aqueous layer was extracted with methylbenzene (2×). The combined organic layers were washed with water, dried, filtered and evaporated. The residue was refluxed for 2 hours in a mixture of 84 parts of acetic acid, 18.4 parts of sulfuric acid and 45 parts of water. After cooling, the whole was diluted with water and extracted with 2,2'-oxybispropane (2×). The combined extracts were washed with NaOH (10%) and water, dried, filtered and evaporated, yielding 22 parts (87.6%) of 1-(4-ethyl-2-nitrophenyl)ethanone (interm. 7).

e) A mixture of 22 parts of intermediate 7,2 parts of a solution of thiophene in methanol 4% and 316 parts of methanol was hydrogenated at normal pressure and 50° C. in the presence of 2 parts of palladium-on-charcoal catalyst 10%. After the calculated amount of hydrogen was taken up, the catalyst was filtered off and the filtrate was evaporated. The residue was purified by column chromatography (silica gel; $CH_2Cl_2$/hexane 80:20). The eluent of the desired fraction was evaporated, yielding 16 parts (89.1%) of 1-(2-amino-4-ethylphenyl)ethanone (interm. 8).

f) A mixture of 5.25 parts of (2,6-dichlorophenyl)methanone, 4.08 parts of intermediate 8 and 105 parts of acetic acid was stirred for 2 hours at room temperature. There were added 1.96 parts of potassium cyanide and stirring was continued for 20 hours. The reaction mixture was poured into water and the product was extracted with dichloromethane. The extract was washed with NaOH (10%) and water, dried, filtered and evaporated. The residue was purified by column chromatography (silica gel; $CH_2Cl_2$/hexane 80:20). The eluent of the desired fraction was evaporated and the residue was crystallized from 2,2'-oxybispropane. The product was filtered off and dried, yielding 4.28 parts (49.3%) of (±)-α-[2-acetyl-5-ethylphenyl)amino]-2,6-dichlorobenzeneacetonitrile; mp. 111.3° C. (interm. 9).

EXAMPLE 5 a) To a solution of 117 parts of (4-trifluoromethylphenyl)methanone in 136 parts of methanol there were added portionwise 13.1 parts of sodium tetrahydroborate under a nitrogen atmosphere, while cooling on ice. After stirring for 18 hours at room temperature, the reaction mixture was poured into water which was acidified with HCl (20%). The product was extracted with 2,2'-oxybispropane (2×) and the combined extracts were washed with water, dried, filtered and evaporated, yielding 130 parts (100%) of 4-(trifluoromethyl)benzenemethanol (interm. 10).

b) A mixture of 125 parts of intermediate 10 and 821 parts of 1-methyl-2-pyrrolidinone was hydrogenated at normal pressure and room temperature in the presence of 3 parts of palladium-on-charcoal catalyst 10%. After the calculated amount of hydrogen was taken up, the catalyst was filtered off and the filtrate was evaporated. The residue was distilled ($1.10^5$ Pa, 90°–100° C.), yielding 75 parts (66.0%) of 1-trifluoromethyl-4-methylbenzene (interm. 11).

c) A mixture of 29.4 parts of intermediate 11 and 4.1 parts of antimony trichloride was stirred for 6 hours at 60° C., while chlorine was bubbled through. The reaction mixture was diluted with 50 parts of water and stirred for another 15 min at 60° C. The product was extracted with 2,2'-oxybispropane and the extract was washed with water, dried, filtered and evaporated. The residue was taken up in hexane and the whole was filtered and evaporated. The residue was distilled ($1.3.10^3$ Pa, 100°–105° C.), yielding 29 parts (61.1%) of 1,3,4-trichloro-5-trifluoromethyl-2-methylbenzene (interm. 12).

d) A mixture of 29 parts of intermediate 12, 30 parts of N-bromosuccinimide, 2.5 parts of benzoylperoxide and 795 parts of tetrachloromethane was stirred for 6 hours at reflux temperature. The reaction mixture was washed with water (2×), dried, filtered and evaporated. The residue was boiled in hexane and the whole was filtered and evaporated, yielding 40 parts (100%) of 2-bromomethyl-1,3,4-trichloro-5-trifluoromethylbenzene (interm. 13).

e) A mixture of 40 parts of intermediate 13,600 parts of water and 27.6 parts of potassium carbonate was stirred for 21 hours at reflux temperature. After cooling, the precipitate was filtered off and recrystallized from hexane. The product was filtered off and dried, yielding 15 parts (48.8%) of 2,3,6-trichloro-4-trifluoromethylbenzenemethanol (interm. 14).

f) To a stirred mixture of 80 parts of water, 79.12 parts of sulfuric acid (conc.) and 1 part of benzyltriethylammonium chloride there were added 6.6 parts of potassium dichromate and dropwise a solution of 15 parts of intermediate 14 in 160 parts of dichloromethane. Stirring at room temperature was continued for 4 hours. The reaction mixture was diluted with 400 parts of water and the product was extracted with dichloromethane (2×). The combined extracts were washed with water, dried, filtered and evaporated, yielding 16 parts (100%) of [2,3,6-trichloro-4-(trifluoromethyl)phenyl]-methanone (interm. 15).

g) A mixture of 4.1 parts of 1-(2-aminophenyl)ethanone, 11 parts of intermediate 15 and 105 parts of acetic acid was stirred for 2 hours at room temperature. There were added 2.6 parts of potassium cyanide and stirring at room temperature was continued for 18 hours. The reaction mixture was poured into 500 parts of water. The product was extracted with dichloromethane (2×) and the combined extracts were washed with Na$_2$CO$_3$ (5%), dried, filtered and evaporated, yielding 16 parts (100%) of 2,3,6-trichloro-4-(trifluoromethyl)-α-[[2-(methylcarbonyl)phenyl]amino] benzeneacetonitrile (interm. 16).

EXAMPLE 6 a) To a stirred mixture of 10 parts of magnesium and 72 parts of tetrahydrofuran there were added portionwise 50 parts of bromocyclopropane, keeping the temperature below 10° C. At reflux temperature, there was added a solution of 50 parts of 2-fluorobenzenecarbonitrile in 72 parts of tetrahydrofuran. Stirring at reflux temperature was continued until completion of the reaction. The reaction mixture was cooled on ice (0°–5° C.) and decomposed with a mixture of ice, water and acetic acid. The product was extracted with trichloromethane (3×) and the combined extracts were washed with water (2×), dried, filtered and evaporated. The residue was distilled (1.33 Pa; 78°–105° C.) (2×), yielding 19.8 parts (29.4%) of cyclopropyl (2-fluorophenyl)methanone; bp. 100°–103° C. (at 1.3 Pa) (interm. 17).

b) To a solution of 50 parts of intermediate 17, 34.5 parts of benzenemethanamine and 218 parts of methylbenzene there were added 45 parts of sodium carbonate. The whole was stirred for 5 days at reflux temperature. The reaction mixture was filtered and the organic layer was separated, washed with water and NaCl(sat.), dried, filtered and evaporated. The residue was triturated in methanol, yielding 32 parts (41.6%) of cyclopropyl[2-[(phenylmethyl)amino]phenyl]methanone (interm. 18).

c) A mixture of 23 parts of intermediate 18 and 223 parts of tetrahydrofuran was hydrogenated at normal pressure and room temperature in the presence of 3 parts of palladium-on-charcoal catalyst 10%. After the calculated amount of hydrogen was taken up, the catalyst was filtered off and the filtrate was evaporated. The residue was purified by column chromatography (silica gel; hexane/(C$_2$H$_5$)$_2$O 90:10). The eluent of the desired fraction was evaporated, yielding 14.1 parts (95.6%) of (2-aminophenyl) cyclopropylmethanone (interm. 19).

d) To a stirred solution of 5 parts of intermediate 19 in 105 parts of acetic acid there were added 6.5 parts of (2,6-dichlorophenyl)methanone and, after 1½ hour, 2.4 parts of potassium cyanide. The whole was stirred for 41 hours at room temperature and then poured into water. The precipitate was filtered off and recrystallized from a mixture of methanol and acetonitrile, yielding 8.5 parts (79.4%) of (±)-2,6-dichloro-α-[[2-(cyclopropylcarbonyl)phenyl]amino]benzeneacetonitrile; mp. 144.1° C. (interm. 20).

B. Preparation of the final compounds

EXAMPLE 7

To 200 parts of a mixture of concentrated sulfuric acid and water (10:1 by volume) there were added portionwise 28.5 parts of intermediate (1). After stirring for 18 hours at room temperature, the reaction mixture was poured into 2000 parts of ice-water. The precipitate was filtered off and dissolved in trichloromethane. This solution was washed with water, dried, filtered and evaporated. The residue was crystallized from 2-propanol. The product was filtered off and dried, yielding 17.2 parts of 2-(2,6-dichlorophenyl)-2-[(2-methoxyphenyl)amino]acetamide; mp. 192° C. (comp. 4).

EXAMPLE 8

To a stirred and cooled (ice-bath) amount of 450 parts of concentrated sulfuric acid there were added portionwise 44 parts of intermediate (2), keeping the temperature below 15° C. The resulting solution was stirred for 3 hours at room temperature and was then poured into 1000 parts of ice-water. The precipitate was filtered off, washed with water, triturated with 2,2'-oxybispropane and recrystallized from acetic acid. The product was filtered off and dried, yielding 24 parts of 2-(2,6-dichlorophenyl)-2-[(2-nitrophenyl)amino]acetamide. Dilution of the mother liquor with water caused a second fraction of product to precipitate. The product was filtered off, washed with petroleumether and dried, yielding an additional 6.6 parts of 2-(2,6-dichlorophenyl)-2-[(2-nitrophenyl)amino]acetamide. Total yield: 30.6 parts; mp. 182.4° C. (comp. 15).

EXAMPLE 9 a) A mixture of 3 parts of intermediate (3) and 50.2 parts of a mixture of concentrated sulfuric acid and water (10/1 by volume) was stirred for 3 hours at room temperature. The reaction mixture was poured into ice-water. The precipitate was filtered off, washed with water and recrystallized from acetonitrile. The product was filtered off and dried, yielding 1.9 parts (59.9%) of (±)-α[(2-acetylphenyl)amino]-2,6-dichlorobenzeneacetamide; mp. 203.9° C. (comp. 22).

b) 0.9 Parts of compound 22 were resolved by column chromatography (Chiracel OD®; hexanes/C$_2$H$_5$OH 80:20). The eluent of the desired fractions was evaporated and the residue was suspended in 2,2'-oxybispropane. The product was filtered off and dried, yielding 0.164 parts (18.2%) of (−)-α-[(2-acetylphenyl)amino]-2,6-dichlorobenzeneacetamide; mp. 168.8° C.; [α]$_D^{20}$=−64.83° (conc.=0.1% in CH$_3$OH) (comp. 23).

EXAMPLE 10

To a stirred solution of 2 parts of compound 22 in 3.5 parts of 2-propanol there were added 0.59 parts of pyridine and 0.5 parts of hydroxylamine monohydrochloride. After stirring for 2 hours at reflux temperature, the reaction mixture was poured into water. The product was extracted with dichloromethane and the extract was washed with water (2×), dried, filtered and evaporated. The residue was successively triturated in petroleum ether and recrystallized from acetonitrile. The product was filtered off and dried, yielding 1.2 parts (56.8%) of (±)-(E)-2,6-dichloro-α-[[2-[1-(hydroxyimino)ethyl]phenyl]amino]benzeneacetamide; mp. 114.8° C. (comp. 35).

EXAMPLE 11

To a stirred solution of 2 parts of compound 22 in 3.5 parts of 2-propanol there were added 0.59 parts of pyridine and 0.6 parts of methoxyamine monohydrochloride. After stirring for 4½ hours at reflux temperature and subsequent cooling, the reaction mixture was poured into water. The precipitate was filtered off, washed with water and crystallized from acetonitrile, yielding 1.2 parts (54.6%) of (±)-(E)-2,6-dichloro-α-[[2-[1-(methoxyimino)ethyl]phenyl]amino]benzeneacetamide; mp. 205.5° C. (comp. 36).

EXAMPLE 12

To a stirred solution of 1.8 parts of compound 22 and 3.12 parts of 2-propanol there were added 0.52 parts of pyridine and 0.32 parts of hydrazine monohydrate. After stirring for 12 hours at reflux temperature, the reaction mixture was extracted with dichloromethane. The extract was washed with water (2×), dried, filtered and evaporated. The residue was purified by column chromatography (silica gel; $CH_2Cl_2$/$CH_3OH$ 95:5). The eluent of the desired fraction was evaporated and the residue was successively triturated in 1,1'-oxybisethane and crystallized from acetonitrile. The product was filtered off and dried, yielding 0.6 parts (32.2%) of (±)-(E)-2,6-dichloro-α-[[2-(1-hydrazinoethyl)phenyl]amino]benzeneacetamide; mp. 175.7° C. (comp. 43).

EXAMPLE 13 a) To a stirred and heated (60° C.) solution of 120 parts of compound (15) in 2100 parts of acetic acid there were added 252 parts of hydrochloric acid. Stirring was continued for 22 hours at 100° C. The reaction mixture was concentrated, the precipitate was filtered off and purified by column chromatography (HPLC; silica gel; $CH_2Cl_2$/$CH_3OH$ 99:1→90:10). The eluent of the desired fraction was evaporated, yielding 48.8 parts (40.6%) of (±)-2,6-dichloro-α-[(2-nitrophenyl)amino]benzeneacetic acid (interm. 21).

b) To a solution of 5.1 parts of intermediate 21 in 66.8 parts of tetrahydrofuran there were added 1.7 parts of N,N-diethylethanamine and dropwise 1.8 parts of ethyl chloroformate. After stirring for 20 min at room temperature, the reaction mixture was poured into 90 parts of $NH_4OH$ (conc.). The solvent was evaporated and the residue was taken up in 298 parts of trichloromethane. The whole was filtered, washed with water (2×), dried, filtered and evaporated. The residue was crystallized from acetonitrile, yielding 1.8 parts (35.2%) of 2,6-dichloro-α-[(2-nitrophenyl)amino]benzeneacetamide (comp. 15).

EXAMPLE 14 a) Through a stirred solution of 5 parts of intermediate 20 and 2.2 parts of N,N-diethylethanamine and 98 parts of pyridine there was bubbled hydrogen sulfide gas until completion of the reaction and then nitrogen gas for 1 hour. The reaction mixture was poured into 200 parts of water and the product was extracted with dichloromethane. The extract was dried, filtered and evaporated. The residue was taken up in trichloromethane and the whole was washed with HCl (dil.) and evaporated. The residue was crystallized from a mixture of methanol and acetonitrile. The product was filtered off and dried in vacuo at 70° C., yielding 4.3 parts (81%) of (±)-2,6-dichloro-α-[(2-cyclopropylcarbonyl)phenyl]amino]benzeneethanethioamide; mp. 222.0° C. (comp. 58).

b) To a stirred and cooled (0° C.) solution of 1 part of compound 58 in 18.8 parts of N,N-dimethylformamide were added 4 parts of a sodium hydroxide solution 2N and 1.3 parts of hydrogen peroxide 30%. After stirring overnight at room temperature, the precipitate was filtered off, washed with water and crystallized from acetonitrile. The product was filtered off and dried in vacuo at 70° C., yielding 0.56 parts (60%) of (±)-2,6-dichloro-α-[[2-(cyclopropylcarbonyl)phenyl]amino]benzeneacetamide; mp. 196.4° C. (comp. 48).

EXAMPLE 15 a) To a solution of 3.7 parts of sodium hydrogen carbonate in 225 parts of water there were added 154 parts of formaldehyde (35% aq.) and 102.0 parts of compound (15). After stirring for 5 hours at reflux temperature and subsequent cooling, the reaction mixture was diluted with 1000 parts of water. The whole was stirred for ½ hour at room temperature. The precipitate was filtered off, washed with water (3×) and crystallized from methanol. The whole was filtered while hot and the filtrate was stirred for 17 hours at room temperature. The crystallized product was filtered off, washed with methanol (2×) and dried in vacuo at 40° C., yielding 76.2 parts (68.6%) of (±)-2,6-dichloro-N-(hydroxymethyl)-α-[(2-nitrophenyl)amino]benzeneacetamide; mp. 175.0° C.

b) The thus obtained derivative was resolved by liquid chromatography using a chiral stationary phase (Chiralcel OJ®). The chromatographic system was deaerated with ethanol. The eluent consisting of ethanol was warmed to a temperature of about 35° C. and was pumped through the system. The racemic compound was dissolved in a mininal amount of ethanol, warmed at 30°–40° C. and injected into the chromatographic system. The desired fractions were collected (UV detection 240 nm) and the solvent was evaporated, yielding the separated enantiomeric derivates.

c) A suspension of 0.53 parts of the obtained residue and 4 parts of 4-methyl-2-pentanone was stirred first for 4 hours at reflux temperature and then for 18 hours at 25° C. The precipitated product was filtered off and the filtrate was further stirred at 25° C. After filtration, the precipitated product was combined with the previous fraction and washed with 0.8 parts of 4-methyl-2-pentanone. The product was filtered off and dried in vacuo at 40° C., yielding a first fraction of 0.17 parts (34.9%) of (−)-2,6-dichloro-α-[(2-nitrophenyl)amino]benzeneacetamide. The filtrate was stirred in an ice bath and evaporated at 40° C., yielding a second fraction of 0.15 parts (30.8%) of (−)-2,6-dichloro-α-[(2-nitrophenyl)amino]benzeneacetamide. Total yield: 0.32 parts (65.7%) of (−)-2,6-dichloro-α-[(2-nitrophenyl)amino]benzeneacetamide (comp. 25) (e.e.=100%).

EXAMPLE 16 a) To a stirred solution of 3.37 parts of N,N,N',N'-tetramethyldiaminomethane in 44 parts of methylbenzene was added dropwise a solution of 2.59 parts of acetylchloride in 26 parts of methylbenzene during 30 minutes at 20°–25° C. under nitrogen atmosphere. Upon completion, the reaction mixture was further stirred for 20 minutes. 10.21 Parts of compound 15 and 78 parts of methylbenzene were added to the previous mixture and stirred for 5 hours at 80° C. The reaction mixture was allowed to cool to 20° C., the precipitated product was filtered off and dried in vacuo at 40° C., yielding 11.66 parts (97.8%) of N-[(dimethylamino)methyl] 2,6-dichloro-α-[(2-nitrophenyl)amino]benzeneacetamide.

b) The thus obtained derivative was resolved by liquid chromatography using a chiral stationary phase (Chiralcel OJ®). The chromatographic system was deaerated with a mixture of hexane and ethanol (80:20; v/v). The eluent consisting of a mixture of hexane and ethanol (80:20; v/v) was warmed to a temperature of about 35° C. and was pumped through the system. The racemic compound was dissolved in a mininal amount of ethanol, warmed at 30°–40° C. and injected into the chromatographic system. The desired fractions were collected (UV detection 240 mm) and the solvent was evaporated, yielding the separated enantiomeric derivates.

c) 0.2 Parts of the desired fraction and 8 parts of 4-methyl-2-pentanone was refluxed for 5 hours in an oil bath at 120° C. The reaction mixture was allowed to cool to 20°–25° C. The precipitated product was filtered off, washed with 2.4 parts of 4-methyl-2-pentanone and dried in vacuo at 40° C. The filtrate was evaporated at 50° C., and purified by column chromatography (HPLC; silicagel; $CH_2Cl_2/CH_3OH$ 99:1→90:10) yielding 0.1 parts (58.8%) of (−)-2,6-dichloro-α-[(2-nitrophenyl)amino]benzeneacetamide (comp. 25) (e.e.=82%).

EXAMPLE 17 a) To a stirred mixture of 585 parts of dichloromethane and 72 parts methanol, saturated with gaseous hydrochloride were added 96.66 parts of intermediate 2. The reaction mixture was stirred for 6.5 hours at 0°–5° C. while bubbling through gaseous hydrochloric acid. After cooling to −10° C., 240 parts of methanol and 260 parts of dichloromethane were added. The reaction mixture was neutralized and alkalized with 365 parts of N,N-diethylethanamine to pH 9. After evaporation in vacuo at 50° C., the residue was stirred in 668 parts of tetrahydrofuran. The precipitate was filtered off, washed with tetrahydrofuran and the filtrate was evaporated to dryness in vacuo at 50° C. The residue was boiled in 280 parts of 2-propanol under nitrogen atmosphere. The product was allowed to crystallize (2 hours, 0°–5° C.), filtered off and washed with 56 parts of 2-propanol, yielding 70.62 parts (66.5%) of (±)-O-methyl 2,6-dichloro-α-[(2-nitrophenyl)amino]benzeneethanimidate.

b) The thus obtained derivative was resolved by liquid chromatography using a chiral stationary phase (Chiralcel OJ®). The chromatographic system was dearrated with ethanol. The eluent consisting of ethanol was warmed to a temperature of about 35° C. and was pumped through the system. The racemic compound was dissolved in a mininal amount of ethanol, warmed at 30°–40° C. and injected into the chromatographic system. The desired fractions were collected (UV detection 240 nm) and the solvent was evaporated, yielding the separated enantiomeric derivates.

c) 0.1 Parts of the above residue were dissolved in 5.6 parts of dichloromethane at 20° C. The whole was heated to 45° C. and a few drops of methanol, saturated with gaseous hydrochloric acid (9.8N) were added. After stirring for 2 hours at reflux temperature (45°–50° C.), the reaction mixture was evaporated to dryness, yielding 0.085 parts (85%) of (−)-2,6-dichloro-α-[(2-nitrophenyl)amino]benzeneacetamide (comp. 25) (e.e.=84%).

EXAMPLE 18 a) To a stirred and cooled (15° C.) solution of 350 parts of 2,6-dichlorobenzaldehyde and 1600 parts of acetic acid was added dropwise a solution of 162.8 parts of potassium cyanide in water during 30 minutes at 15°–20° C. After stirring for 16 hours at 20° C., 1300 parts of dichloromethane and 1000 parts of water were added. The separated aqueous layer was washed three times with dichloromethane. The combined organic layers were washed with water, dried, filtered and evaporated at 40° C., yielding 396 parts of 2,6-dichloro-α-hydroxybenzeneacetonitrile.

b) 396 Parts of the above product were combined with 80 parts of methanol and stirred at 20° C. 800 Parts of methanol, saturated with ammonia were added and the whole was refluxed for 4 hours (40° C.→60° C.). After evaporation in vacuo, the residue was taken up in 520 parts of dichloromethane and 200 parts of water. The separated organic layer was washed twice with 200 parts of water, dried and cooled to 10° C. The whole was acidified with 280 parts of 2-propanol, saturated with hydrochloric acid. The crystallized product was filtered off, taken up in 390 parts of dichloromethane and 200 parts of water and saturated with ammonia to pH>9. The separated organic layer washed with 200 parts of water, dried, filtered and evaporated, yielding 245 parts of α-amino-2,6-dichlorobenzeneacetonitrile.

c) The thus obtained derivative was resolved by liquid chromatography using a chiral stationary phase (Chiralcel OJ®). The chromatographic system was deaerated with a mixture of hexane and ethanol (80:20; v/v). The eluent consisting of a mixture of hexane and ethanol (80:20; v/v) was pumped through the system. The racemic compound was dissolved in a mininal amount of ethanol and injected into the chromatographic system. The desired fractions were collected (UV detection 240 nm) and the solvent was evaporated, yielding the separated enantiomeric derivates.

d) The separated enantiomeric derivate was stirred in 52 parts of dichloromethane at 10°–15° C. 2-Propanol, saturated with hydrochloric acid was added and after stirring for 1 hour at 20° C., the precipitated product was filtered off, washed with 26 parts of dichloromethane and taken up in 260 parts of dichloromethane and 100 parts of water. The solution was treated with ammonia to pH>9. The separated organic layer was washed, dried and dissolved in 280 parts of dichloromethane. After cooling to 0° C., 26.8 parts of sulfuric acid were added dropwise. The whole was stirred for 18 hours at 20° C. and 100 parts of water were added. The reaction mixture was treated with ammonium hydroxide at <20° C. The separated aqueous layer was extracted twice with dichloromethane. The combined dichloromethane layers were washed with water, dried, filtered and evaporated at <45° C., yielding 8.1 parts (82.6%) of α-amino-2,6-dichlorobenzeneacetamide.

e) A mixture of 0.092 parts of α-amino-2,6-dichlorobenzeneacetamide, 0.032 parts of 2-fluoronitrobenzene and 1 part of 1,3-dimetyl-2-imidazolidinone was stirred for 6 hours at 140° C. The product was extracted and the extract was dried, filtered and evaporated at 100° C. and 133–266 Pa. The residue was purified by column chromatography (HPCL; silica gel; $CH_2Cl_2/CH_3OH$ 99:1→90:10), yielding 0.12 parts of (−)-2,6-dichloro-α-[(2-nitrophenyl)amino]benzeneacetamide (e.e.=90%).

All other compounds in the following table were prepared following the procedures described in Examples 7–18.

TABLE 1

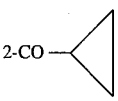

| Co. No. | R⁵ | R⁶ | R⁸ | R⁹ | R¹⁰ | Physical data |
|---|---|---|---|---|---|---|
| 1 | 6-Cl | H | H | H | H | mp. 148.5° C. |
| 2 | 6-Cl | H | 3-CH₃ | H | H | mp. 163.5° C. |
| 3 | 6-Cl | H | 3-Cl | H | H | mp. 147° C. |
| 4 | 6-Cl | H | 2-OCH₃ | H | H | mp. 192° C. |
| 5 | 6-Cl | H | 3-NO₂ | H | H | mp. 230° C. |
| 6 | 6-Cl | H | 3-CH₃ | 4-CH₃ | H | mp. 170.5° C. |
| 7 | 6-Cl | H | 4-CH₃ | H | H | mp. 148° C. |
| 8 | 6-Cl | H | 2-CH₃ | 5-CH₃ | H | mp. 186° C. |
| 9 | 6-Cl | H | 2-OH | 5-CH₃ | H | mp. 197.5° C. |
| 10 | 6-Cl | H | 2-OCH₃ | 5-CH₃ | H | mp. 197° C. |
| 11 | 6-Cl | 3-NO₂ | H | H | H | mp. 174.6° C. |
| 12 | 6-Cl | 3-NO₂ | 2-CH₃ | H | H | mp. 174.1° C. |
| 13 | 6-Cl | 3-NO₂ | 3-Cl | H | H | mp. 77.9° C. |
| 14 | 4-Cl | H | 2-Cl | 6-Cl | H | mp. 158.6° C. |
| 15 | 6-Cl | H | 2-NO₂ | H | H | mp. 182.4° C. |
| 16 | H | H | 2-Cl | 4-Cl | H | mp. 168° C. |
| 17 | 6-Cl | H | 3-Cl | 5-Cl | H | mp. 180.9° C. |
| 18 | 4-Cl | H | 2-Cl | 4-NO₂ | H | mp. 198.8° C. |
| 19 | 6-Cl | H | 2-Cl | H | H | mp. 166° C. |
| 20 | 3-Cl | 6-Cl | 2-OCH₃ | H | H | mp. 198.8° C. |
| 21 | 6-Cl | H | 2-CONH₂ | H | H | mp. 258.0° C. |
| 22 | 6-Cl | H | 2-COCH₃ | H | H | mp. 203.9° C. |
| 23 | 6-Cl | H | 2-COCH₃ | H | H | mp. 168.8° C. $[\alpha]_{D\ 0.1\%\ CH_3OH}^{20} = -64.83°$ |
| 24 | 6-Cl | H | 2-NO₂ | 4-CH₃ | 5-CH₃ | mp. 242.2° C. |
| 25 | 6-Cl | H | 2-NO₂ | H | H | mp. 193.3° C. $[\alpha]_{D\ 0.1\%\ CH_3OH}^{20} = -373.74°$ |
| 26 | 6-Cl | H | 2-NO₂ | 5-CH₃ | H | mp. 236.2° C. |
| 27 | 6-Cl | H | 2-NO₂ | 3-CH₃ | 5-CH₃ | mp. 215.1° C. |
| 28 | 3-Cl | 6-Cl | 2-NO₂ | 4-CH₃ | 5-CH₃ | mp. 235.2° C. |
| 29 | 6-Cl | H | 2-NO₂ | 5-CH₃ | H | mp. 224.5° C. $[\alpha]_{D\ 0.1\%\ CH_3OH}^{20} = -371.91°$ |
| 30 | 6-Cl | H | 2-COCH₃ | 5-Cl | H | mp. 250.2° C. |
| 31 | 6-Cl | H | 2-COCH₃ | 5-CH₃ | H | mp. 226.1° C. |
| 32 | 6-Cl | H | 2-COCH₃ | 5-F | H | mp. 215.0° C. |
| 33 | 6-Cl | H | 2-OCF₃ | H | H | mp. 119.0° C. |
| 34 | 6-Cl | H | 2-OCH₃ | 3-CH₃ | H | mp. 199.4° C. |
| 35 | 6-Cl | H | 2-C(CH₃)=NOH | H | H | mp. 114.8° C. |
| 36 | 6-Cl | H | 2-C(CH₃)=NO—CH₃ | H | H | mp. 205.5° C. |
| 37 | 3-Cl | 6-Cl | 2-COCH₃ | 5-CH₃ | H | mp. 193.3° C. |
| 38 | 6-Cl | H | 2-COCH₃ | 4-CH₃ | 5-CH₃ | mp. 215.2° C. |
| 39 | 6-Cl | H | 2-OCH₃ | 3-C₃H₇n | 5-CH₃ | mp. 148.5° C. |
| 40 | 3-Cl | 6-Cl | 2-COCH₃ | 4-CH₃ | 5-CH₃ | mp. 203.8° C. |
| 41 | 6-Cl | H | 2-COCH₃ | 5-COCH₃ | H | mp. 235.3° C. |
| 42 | 6-Cl | H | 2-Cl | 5-COCH₃ | H | mp. 216.9° C. |
| 43 | 6-Cl | H | 2-C(CH₃)=NNH₂ | H | H | mp. 175.7° C. |
| 44 | 6-Cl | H | 2-COCH₃ | 5-C₂H₅ | H | mp. 169.2° C. |
| 45 | 6-Cl | H | 2-COCH₃ | 5-CH₃ | H | mp. 203.6° C. $[\alpha]_{D\ 0.951\ in\ CH_3OH}^{20} = +15.77°$ |
| 46 | 6-Cl | H | 2-COCH₃ | 5-CH₃ | H | mp. 189.5° C. $[\alpha]_{D\ 1.046\ in\ CH_3OH}^{20} = -14.34°$ |
| 47 | 6-Cl | H | 2-COCH₃ | 3-OCH₃ | H | mp. 201.6° C. |
| 48 | 6-Cl | H | 2-CO—△ | H | H | mp. 196.4° C. |
| 49 | 4-Br | 6-Cl | 2-COCH₃ | H | H | |
| 50 | 4-CN | 6-Cl | 2-COCH₃ | H | H | |
| 51 | 4-COOH | 6-Cl | 2-COCH₃ | H | H | |

TABLE 1-continued

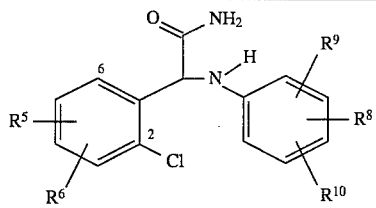

| Co. No. | R⁵ | R⁶ | R⁸ | R⁹ | R¹⁰ | Physical data |
|---|---|---|---|---|---|---|
| 52 | 4-COOCH₃ | 6-Cl | 2-COCH₃ | H | H | |
| 53 | 4-CONH₂ | 6-Cl | 2-COCH₃ | H | H | |
| 54 | 4-COCH₃ | 6-Cl | 2-COCH₃ | H | H | |
| 55 | 4-CF₃ | 6-Cl | 2-COCH₃ | H | H | |
| 56 | 4-CH₂NH₂ | 6-Cl | 2-COCH₃ | H | H | |

TABLE 2

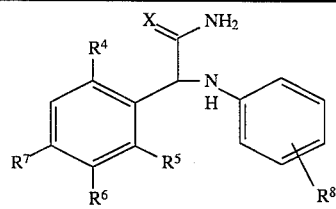

| Co. No. | R⁴ | R⁵ | R⁶ | R⁷ | R⁸ | X | Physical data |
|---|---|---|---|---|---|---|---|
| 57 | Br | Br | H | H | 2-NO₂ | O | mp. 216.1° C. |
| 58 | Cl | Cl | H | H | 2-CO—△ | S | mp. 222.0° C. |
| 59 | Cl | Cl | Cl | CF₃ | 2-COCH₃ | O | mp. 230.9° C. |

C. Pharmacological example

EXAMPLE 19

A rapid, sensitive and automated assay procedure was used for the in-vitro evaluation of anti-HIV agents. An HIV-1 transformed T4-cell line, MT-4, which was previously shown (Koyanagi et al., Int. J. Cancer, 36, 445–451, 1985) to be highly susceptible to and permissive for HIV infection, served as the target cell line. Inhibition of the HIV-induced cytopathic effect was used as the end point. The viability of both HIV-and mock-infected cells was assessed spectrophotometrically via the in-situ reduction of 3-(4,5-dimethylthiazol-2-yl)-2,5-diphenyltetrazolium bromide (MTT). The 50% cytotoxic dose ($CD_{50}$ in μg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% effective dose ($ED_{50}$ in μg/ml). The ratio of $CD_{50}$ to $ED_{50}$ was defined as the selectivity index (SI). All compounds of the table hereinabove were shown to have a selectivity index larger than 1, i.e. inhibit HIV-1 effectively at doses below the cytotoxic dose. Particular values are listed in the table hereinbelow.

| Co. No. | $CD_{50}$ (μg/ml) | $ED_{50}$ (μg/ml) | SI |
|---|---|---|---|
| 15 | 20 | 0.02 | ~1000 |
| 22 | 35 | 0.013 | ~2700 |
| 23 | 20 | 0.0066 | ~3000 |
| 24 | 160 | 0.077 | ~2100 |
| 25 | 29 | 0.018 | ~1600 |
| 26 | >250 | 0.057 | ≧4400 |
| 27 | 5 | 0.049 | ~100 |
| 28 | 10 | 0.07 | ~140 |
| 29 | 5 | 0.0032 | ~1550 |
| 30 | 200 | 0.011 | ~18000 |

We claim:

1. A method of treating subjects suffering from HIV-1 infection which comprises administering to said subjects an effective anti-HIV-1 amount of a compound of the formula:

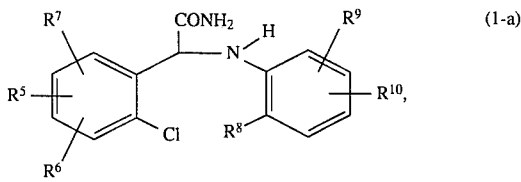

a pharmaceutically acceptable acid addition salt form or a stereochemically isomeric form thereof, wherein:

$R^5$ and $R^6$ each independently are hydrogen, halo, $C_{1-6}$alkyl, $C_{1-6}$alkyloxy, nitro, trifluoromethyl, cyano, aminomethyl, carboxyl; $C_{1-4}$alkyloxycarbonyl, $C_{1-4}$alkylcarbonyl, aminocarbonyl or hydroxy;

$R^7$ is hydrogen or halo;

$R^8$ represents $C_{1-6}$alkyloxy, nitro, trifluoromethoxy, 2,2,2-trifluoroethoxy, (trifluoromethyl)carbonyl, aminocarbonyl, (cyclopropyl)carbonyl, or a radical of the formula $C_{1-6}$alkyl-(C=Y)— wherein =Y represents =O, =N—OH, =N—OCH₃, =N—NH₂, or =N—N(CH₃)₂;

$R^9$ and $R^{10}$ each independently are hydrogen, halo, $C_{1-6}$alkyl, $C_{1-6}$alkyloxy, nitro, hydroxy, trifluoromethoxy, 2,2,2-trifluoroethoxy, (trifluoromethyl)carbonyl, aminocarbonyl, (cyclopropyl)carbonyl or a radical of the formula $C_{1-6}alkyl\text{-}(C=Y)-$ wherein $=Y$ represents $=O$, $=N-OH$, $=N-OCH_3$, $=N-NH_2$, or $=N-N(CH_3)_2$, provided that $R^8$ is other than 2-methoxy when $R^5$ is 6-chloro, $R^6$, $R^7$ and $R^9$ are hydrogen and $R^{10}$ is hydrogen or 5-methyl.

2. A method as claimed in claim 1 wherein $R^5$ and $R^6$ are each independently hydrogen, halo, $C_{1-6}$alkyloxy or nitro; $R^7$ is hydrogen; $R^8$ is $C_{1-6}$alkyloxy, nitro, trifluoromethoxy or $C_{1-6}$alkylcarbonyl; and $R^9$ and $R^{10}$ are each independently hydrogen, halo, $C_{1-6}$alkyl, $C_{1-6}$alkyloxy, nitro, trifluoromethoxy or $C_{1-6}$alkylcarbonyl.

3. A method as claimed in claim 2 wherein $R^5$ and $R^6$ are each independently hydrogen, halo, methoxy or nitro; $R^8$ is methoxy, nitro, trifluoromethoxy or methylcarbonyl; and $R^9$ and $R^{10}$ are each independently hydrogen, halo, methyl, methoxy, nitro, trifluoromethoxy or methylcarbonyl.

4. A method as claimed in claim 3 wherein $R^5$ represents 6-chloro, and $R^6$ and $R^7$ represent hydrogen; or $R^5$ and $R^6$ represent 3,6-dichloro and $R^7$ represents hydrogen.

5. A method as claimed in claim 4 wherein $R^8$ represents 2-methoxy, 2-nitro, 2-methylcarbonyl, or 2-trifluoromethyl; and $R^9$ and $R^{10}$ represent hydrogen; or $R^8$ and $R^9$ represent 2-methoxy-5-methyl, 2-nitro-5-chloro, 2-nitro-5-methyl, 2-methoxy-5-chloro, 2-methylcarbonyl-5-methyl, 2-methylcarbonyl-5-fluoro or 2-methylcarbonyl-5-chloro; and $R^{10}$ represents hydrogen.

6. The method of claim 1 wherein the compound is (±)-α-[(2-acetyl-5-methylphenyl)amino]-2,6-dichlorobenzeneacetamide.

7. The method of claim 1 wherein the compound is (−)-α-[(2-acetyl-5-methylphenyl)amino]-2,6-dichlorobenzeneacetamide.

8. A method as defined in claim 1 wherein said compound is selected from the group consisting of:

(−)-α-[(2-nitrophenyl)amino]-2,6-dichlorobenzeneacetamide;

(−)-α-[(5-methyl-2-nitrophenyl)amino]-2,6-dichlorobenzeneacetamide;

(−)-α-[(2-acetylphenyl)amino]-2,6-dichlorobenzeneacetamide;

(−)-α-[(2-acetyl-5-methylphenyl)amino]-2,6-dichlorobenzeneacetamide;

α-[(2-acetyl-5-chlorophenyl)amino]-2,6-dichlorobenzeneacetamide;

α-[(5-chloro-2-nitrophenyl)amino]-2,6-dichlorobenzeneacetamide; and

α-[(2-acetyl-5-fluorophenyl)amino]-2,6-dichlorobenzeneacetamide.

9. A pharmaceutical composition comprising a pharmaceutically acceptable carrier and as active ingredient an anti-HIV-1 effective amount of a compound as defined in claim 1.

10. A pharmaceutical composition as defined in claim 9 wherein said compound is selected from the group consisting of:

(−)-α-[(2-nitrophenyl)amino]-2,6-dichlorobenzeneacetamide;

(−)-α-[(5-methyl-2-nitrophenyl)amino]-2,6-dichlorobenzeneacetamide;

(−)-α-[(2-acetylphenyl)amino]-2,6-dichlorobenzeneacetamide;

(−)-α-[(2-acetyl-5-methylphenyl)amino]-2,6-dichlorobenzeneacetamide;

α-[(2-acetyl-5-chlorophenyl)amino]-2,6-dichlorobenzeneacetamide;

α-[(5-chloro-2-nitrophenyl)amino]-2,6-dichlorobenzeneacetamide; and

α-[(2-acetyl-5-fluorophenyl)amino]-2,6-dichlorobenzeneacetamide.

11. The pharmaceutical composition of claim 9 wherein said compound is (±)-α-[(2-acetyl-5-methylphenyl)amino]-2,6-dichlorobenzeneacetamide.

12. The pharmaceutical composition of claim 9 wherein said compound is (−)-α-[(2-acetyl-5-methylphenyl)amino]-2,6-dichlorobenzeneacetamide.

\* \* \* \* \*